United States Patent [19]

Denen et al.

[11] Patent Number: 4,893,013

[45] Date of Patent: Jan. 9, 1990

[54] DETECTOR AND LOCALIZER FOR LOW ENERGY RADIATION EMISSIONS

[75] Inventors: Dennis J. Denen; Marlin O. Thurston; Raymond C. Ramsey, all of Columbus, Ohio

[73] Assignee: Neoprobe Corporation, Columbus, Ohio

[21] Appl. No.: 248,920

[22] Filed: Sep. 23, 1988

Related U.S. Application Data

[63] Continuation-in-part of Ser. No. 27,197, Mar. 17, 1987, Pat. No. 4,801,803.

[51] Int. Cl.[4] ............................................. G01T 1/161
[52] U.S. Cl. ................................. 250/336.1; 128/659; 250/370.01
[58] Field of Search .......................... 128/659, 654; 250/370.07, 370.01, 336.1

[56] References Cited

U.S. PATENT DOCUMENTS

| | | | |
|---|---|---|---|
| 3,669,095 | 6/1972 | Kobayashi et al. | 128/659 |
| 4,782,840 | 11/1988 | Martin, Jr. et al. | 128/654 |
| 4,801,803 | 1/1989 | Denen et al. | 250/336.1 |

FOREIGN PATENT DOCUMENTS

| | | | |
|---|---|---|---|
| 1515552 | 1/1968 | France | 128/659 |
| 2155773 | 5/1973 | France | 128/659 |
| 728868 | 4/1980 | U.S.S.R. | 128/659 |

*Primary Examiner*—Constantine Hannaher
*Attorney, Agent, or Firm*—Mueller and Smith

[57] ABSTRACT

A detector particularly suited for use in immuno-guided surgery capable of detecting very faint gamma emissions and thereby localizing cancerous tumor. The detector employs a hand manipular probe within which is contained a crystal such as cadmium telluride which is secured in a light-tight environment. A noise immune structuring of the probe and crystal combination includes the utilization of a resilient compressible shock cushion layer located at one face of the crystal in conjunction with a biasing surface. Additionally, an elastomeric retainer is positioned over the assemblage of crystal, cup, and shock cushion layer to form a sub-assembly for retention within the device. A dead air space is developed between the forward facing window of the probe and the crystal remaining assemblage.

5 Claims, 4 Drawing Sheets

DETECTOR AND LOCALIZER FOR LOW ENERGY RADIATION EMISSIONS

CROSS REFERENCE TO RELATED APPLICATION

This application is a continuation-in-part of application Ser. No. 07/027,197, filed Mar. 17, 1987, "Detector and Localizer for Low Energy Radiation Emissions", by Denen, et al., now U.S. Pat. No. 4,801,803, issued Jan. 31, 1989 and assigned in common herewith.

BACKGROUND

The detection and treatment of cancerous tissue has been the subject of intense investigation for many years. One among the many approaches to its detection has concerned the identification of tumor specific antigens. Where these antigens can be identified, radionucleid labeled antibodies have been employed which tend to collect at tumor sites. When so concentrated, somewhat elaborate radiation detection equipment then is employed to record, for example, by imaging the concentrations of the emissive substances and thus to locate neoplastic tissue. Important advances in this procedure have been evidenced through the use of monoclonal antibodies or fragments thereof with a variety of radionucleides. Typical techniques for carrying out imaging of these antibodies have involved, for example, tomographic scanning, immunoscintigraphy and the like. The particular choice of radionucleid for labeling antibodies is dependent upon its nuclear properties, the physical half life, the detection instrument capabilities, the pharmacokinetics of the radiolabeled antibody, and the degree of difficulty of the labeling procedure. The most widely used of these radionucleides in nuclear medicine imaging include technetium, $^{99m}Tc$, iodine $^{125}I$, $^{131}I$, and indium, $^{111}In$. Of the above, for localizing tumors of the gastro-intestinal tract, the radionucleid $^{131}I$ is used as the marker or label in conjunction with imaging gamma cameras and the like which are relatively large and elaborate devices positioned above the patient during the imaging process.

In spite of its somewhat extensive utilization, $^{131}I$ is not an ideal radionucleid for use in diagnostic medicine. The high energy gamma-photon emitted from $^{131}I$ is poorly detected by the classic gamma camera and like instrumentation. In addition, the administered marker emissions deliver a high radiation dose to the patient. Further, the imaging definition of these external imaging devices have not been satisfactory for many reasons. As tumor sites become smaller, the radionucleid concentrations thereat will tend to be lost, from an imaging standpoint, in the background or blood pool radiation necessarily present in the patient.

Over the recent past, a surgical procedure has been developed concerning the differentiation and removal of such neoplastic tissue through the use of much lower energy gamma emission levels for example, $^{125}I$(27–35 kev). While such a radiolabel cannot be employed with conventional external imaging or scanning devices because the radiation is strongly absorbed by the tissue intermediate between the tumor and the surface of the patient's body, it has been found that when employed with a probe type detection structure, a highly effective differentiation technique can be evolved. More particularly, the longer half life of this type of radiolabel coupled with a surgical methodology involving the waiting of appropriate intervals from the time of introduction of the radiolabelled antibody to the patient to the time of surgery, can evolve a highly accurate differentiation of cancerous tumor. This improved method of localization, differentiation and removal of cancerous tumor involves a surgical procedure wherein the patient suspected of containing neoplastic tissue is administered an effective amount of a labeled antibody specific for neoplastic tissue and labeled with a radioactive isotope as above-noted exhibiting photon emissions of specific energy levels. Next, the surgical procedure is delayed for a time interval following such administration for permitting the labeled antibody to preferentially concentrate in any neoplastic tissue present in the patient to be cleared from normal tissue so as to increase the ratio of photon emissions from the neoplastic tissue to the background photon emissions. Thereafter, an operative field of the patient is surgically accessed and tissue within the operative field to be examined for neoplastic tissue has the background photon emission count determined. Once the background photon emission count for the tissue within the operative field has been determined, this hand-held probe is manually positioned within the operative field adjacent tissue suspected of being neoplastic. Readouts then can be achieved from probe counting for differentiation. In the above regard, reference is made to the following technical publications:

I. "CEA-Directed Second-Look Surgery in the Asymtomatic Patient after Primary Resection of Colorectal Carcinoma", E. W. Martin, Jr., MD, J. P. Minton, MD, PhD, Larry C. Carey, MD. Annals of Surgery 202:1 (September 1985 301–12.

II. "Intraoperative Probe-Directed Immunodetection Using a Monoclonal Antibody", P. J. O'Dwyer, MD, C. M. Mojzsik, RN MS, G.H. Hinkle, RPh, MS, M. Rousseau, J. Olsen, MD, S. E. Tuttle, MD, R. F. Barth, PhD, M. O. Thurston, PhD, D. P. McCabe, MD, W. B. Farrar, MD, E. W. Martin, Jr., MD. Archives of Surgery, 121 (December 1986) 1321–1394.

III. "Intraoperative Radioimmunodetection of Colorectal Tumors with a Hand-Held Radiation Detector", D. T. Martin, MD, G. H. Hinkle, MS RPh, S. Tuttle, MD, J. Olsen, MD, H. Abdel-Nabi, MD, D. Houchens, PhD, M. O. Thurston, PhD, E. W. Martin, Jr., MD. American Journal of Surgery, 150:6 (December 1985) 672–75.

IV. "Portable Gamma Probe for Radioimmune Localization of Experimental Colon Tumor Xenografts", D. R. Aitken, MD, M. O. Thurston, PhD, G. H. Hinkle, MS RPh, D. T. Martin, MD, D. E. Haagensen, Jr., MD, PhD, D. Houchens, PhD, S. E. Tuttle, MD, E. W. Martin, Jr., MD. Journal of Surgical Research, 36:5 (1984) 480–489.

V. "Radioimmunoguided Surgery: Intraoperative Use of Monoclonal Antibody 17-1A in Colorectal Cancer". E. W. Martin, Jr., MD, S. E. TUttle, MD, M. Rousseau, C. M. Mojzisik, RN MS, P. J. O'Dwyer, MD, G. H. Hinkle, MS RPh, E. A. Miller, R. A. Goodwin, O. A. Oredipe, MA, R. F. Barth, MD, J. O. Olsen, MD, D. Houchens, PhD, S. D. Jewell, MS, D. M. Bucci, BS, D. Adams, Z. Steplewski, M. O. Thurston, PhD, Hybridoma, 5 Suppl 1 (1986)S97-108.

Reference further is made to commonly assigned application for U.S. patent application Ser. No. 06/905,880 entitled "Method for Locating, Differentiating, and Removing Neoplasms" by Edward W. Martin, Jr., and Marlin O. Thurston, filed Sept. 10, 1986, now U.S. Pat. No. 4,782,640, issued Nov. 8, 1988.

The success of this highly effective differentiation and localization technique is predicated upon the availability of a probe-type detecting device capable of detecting extremely low amounts of radiation necessarily developed with the procedure. In this regard, low energy radionucleides are used such as $^{125}I$ and the distribution of radiolabeled antibody with the nucleid is quite sparse so that background emissions can be minimized and the ratio of tumor-specific counts received to background counts can be maximized. Conventional radiation detection probe-type devices are ineffective for this purpose. Generally, because a detection device is required for the probes which is capable of performing at room temperatures, a detection crystal such as cadmium telluride is employed. The probe using such a crystal must be capable of detecting as little as a single gamma ray emission which may, for example, create electron-hole pairs in the crystal of between about 2,000 and 4,000 electrons. Considering that an ampere generates $6.25 \times 10^{18}$ electrons per second, one may observe that extremely small currents must be detectable with such a probe. However, the probe system also must be capable of discriminating such currents from any of a wide variety of electrical disturbances, for example which may be occasioned from cosmic inputs, room temperature molecular generated noise, and capacitively induced noise developed from the mere manipulation of the probe itself. While being capable of performing under these extreme criteria, the same probe further must be capable of performing under the requirements of the surgical theater. In this regard, it must be sterilizable and rugged enough to withstand manipulation by the surgeon within the operating room environment. Further, the system with which the probe is employed, must be capable of perceptively apprising the surgeon of when neoplastic tissue is being approached such that the device may be employed for the purpose of guiding the surgeon to the situs of cancer. Additionally, for surgical use, the probe instrument must be small, so as to be effectively manipulated through surgical openings and the like. Such dimunitive size is not easily achieved under the above operational criteria. This technique has been described as "radioimmuno-guided surgery", a surgical approach developed by E. W. Martin, Jr., MD, and M. O. Thurston, PhD.

In addition to the capability of performing under the above-noted extreme criteria, the probe instrument called upon for the instant use preferably should be fabricable employing practical manufacturing techniques.

SUMMARY

The present invention is addressed to apparatus and system for detecting and locating sources of emitted radiation and, particularly, sources of gamma radiation. Detection is achieved under room temperature conditions using a crystal such as cadmium telluride and with respect to very low energy emissions. To achieve the extreme sensitivity capabilities of the apparatus, an instrumentation approach has been developed in which the somewhat fragile crystal is securely retained in isolation from externally induced incidents otherwise creating excessive noise. In this regard, microphonic effects are minimized through employment of a sequence of materials exhibiting divergent acoustic impedances. Capacitive effects occasioned by the most minute of intercomponent movements are controlled to acceptable levels. The instrument also achieves performance while being structured for assembly by practical manufacturing techniques.

The probe instrument design incorporates a preamplifier with an integrator structure which resides in substantial adjacency with the crystal within the probe instrument and which achieves very substantial amplifying gain of relatively minute crystal derived charge signals. This sensitivity permits medical uses of the instrument, for example, in immuno-guided surgery where low energy gamma emissions are located to differentiate cancerous tumor.

A feature of the invention provides an instrument for detecting and localizing sources of radiation emission having predetermined energy levels which includes a housing having an interior wall defining an interior cavity and a first portion having sidewalls formed of select gamma radiation attenuating material and exhibiting an electrical and radiation shielding effect, and extending to a forward opening positionable proximate the source of radiation and a hand-graspable second portion extending from the first portion. A window permitting transmission of gamma radiation of energy level at least as low as 27 kev through the forward opening which also serves to block the passage of light is provided. A blocking arrangement formed of material selected for attenuating gamma radiation of the predetermined energy levels having an outer surface is supportable within the housing and has a portion extensible within the housing first portion to a base support surface. An elastomer is located intermediate the housing and the blocking arrangement for retaining the blocking arrangement spaced from the housing interior wall. An electrically insulative support arrangement is mounted upon the blocking arrangement base support surface and has a mounting surface positioned outwardly from the base support surface. Further, a resiliently compressible shock cushion layer is positioned in adjacency over the insulative support and has an outwardly disposed surface. A gamma radiation responsive crystal is provided having a rearwardly disposed surface positioned in adjacency with the shock cushion layer and has a forwardly disposed surface. An arrangement for electrically grounding the crystal forwardly disposed surface is provided and a biasing arrangement for applying an electrical bias to the crystal rearwardly disposed surface also is provided. An elastomeric retainer is positioned over the assemblage of the support, the shock cushion layer, and the crystal for effecting their compressed mutual association and, a retainer arrangement is provided for positioning the housing first portion over the assemblage and the blocking arrangement portion such that the crystal forwardly disposed surface is spaced from the window an amount establishing a dead air space therebetween.

Other objects of the invention will, in part, be obvious and will, in part, appear hereinafter.

The invention, accordingly, comprises the apparatus and system possessing the construction, combination of elements and arrangement of parts which are exemplified in the following detailed disclosure. For a fuller understanding of the nature and objects of the invention, reference should be had to the following detailed description taken in connection with the accompanying drawings.

DETAILED DESCRIPTION OF THE INVENTION

Figure 1:
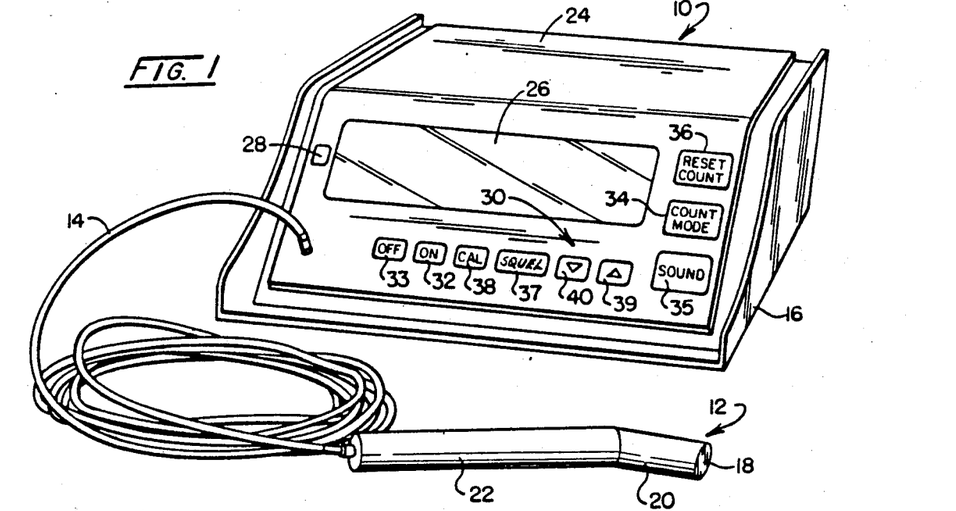
FIG. 1 is a perspective view of the probe instrument and associated console representing the instrumentation system of the invention.

Referring to FIG. 1, an embodiment of the probe and supporting instrumentation of the invention particularly designed for employment in the medical-surgical field is represented generally at 10. This assemblage includes a hand-manipular probe represented generally at 12 which is coupled by a triaxial cable 14 to a console 16. The probe 12, which preferably is retained by the surgeon within a disposable polymeric sheath or cover is maneuvered about the region of surgical interest to locate tumorous tissue for resection. When used in conjunction with colonic surgery, for example, the probe 12 is maneuvered through a surgical opening in the body cavity and essentially brought into contact with organs under study by the surgeon. When employed in a radioimmuno-guided mode, a loudspeaker or annunciator within the console 16 may be employed to provide a "siren" form of output which apprises the surgeon that the probe 12 is at a site of cancer. Thus, it is necessary that the device 12 be of convenient length and comfortable to grasp. The probe 12 is seen to include a window 18 located at the tip of an angularly oriented portion thereof 20. Portion 20 extends from a hand-grippable portion 22 at an angle of about 30° to facilitate its maneuverability about the back or hidden side of organs.

Because the assemblage 10 is used in a surgical theater, the console 16 also is readily cleaned, having a smooth, one-piece touch sensitive polymeric surface 24 surmounting a relatively large LCD readout or display 26, a dual colored LED readout 28 and a sequence of finger-actuated switches having a tactile feedback. These switches or keyboard as represented generally at 30 permit the microprocessor driven console 16 to carry out an instructive or "user friendly" dialogue with the practitioner. For purposes of safety, the device is powered by a rechargeable battery.

In addition to conventional on and off switches shown, respectively, at 32 and 33, the switches provided on the console 16 include a count mode switch 34, a sound switch 35, a reset count switch 36, a squelch function switch 37, a calibration function switch 38, and up and down incrementing switches for adjustment within certain of the switch generated modes as shown, respectively, at 39 and 40.

The probe 12 must be capable of performing essentially at room temperature. Thus, the device employs a cadmium telluride crystal and, because of the preferred low energy levels of radiation which it is called upon to detect, must be capable of operatively reacting to low energy gamma ray interactions. The interaction of gamma rays with such crystals is primarily through three processes, namely the photo-electric effect, Compton scattering, and pair production. In the photo-electric effect, a photon of energy, hv, interacts with an atom as a whole. Its energy is completely transferred to an electron, usually in the innermost shell. The electron is ejected with a kinetic energy: $e_{kin} = hv - E_b$ is the binding energy of the orbital electron, h is Planck's constant, and v is the frequency associated with the wave nature of the gamma radiation. Such electrons undergo many collisions until this energy is shared with some thousands of other electrons. Each of these electrons leaves behind a positively charged region called in the literature a "hole". At the energies of $^{125}I$ Compton scattering is of minor importance. Pair production refers to the reaction of an electron and a photon by the gamma ray. Since this process requires more than 1.0 Mev it does not occur in the present application. In Compton scattering, the primary photon may interact with any one of the orbital electrons. The electrons are considered essentially as free electrons under the condition that the primary photon energy is large compared with the electron binding energy. The interaction may be analyzed as the elastic collision between the primary photon and the electron. Energy is shared between the recoil electron and the secondary photon. This secondary photon travels in a direction different from that of the primary photon, and is referred to as the scattered photon.

Thus, as an incoming gamma ray is absorbed by the crystal, it transfers some or all of its energy to electrons, which as charged particles pass through the semi-conductor producing electron-hole pairs and, therefore, the capability of charge-transfer within the crystal medium.

When a charge particle produces electron-hole pairs in the semi-conductor, the electric field causes these charge carriers to move toward and accumulate at the appropriate electrodes. As these charges move toward or are collected at the electrodes, they induce a charge or electrical pulse signal in the circuit external to the detector. It is then necessary to pre-amplify these signals and feed them to the electronics of the control unit or console 16.

For effective performance, the probe 12 must be capable of generating and discerning signals representing gamma ray strikes which are of extremely low energy. In this regard, a gamma ray interaction with the cadmium telluride crystal may produce two to four thousand electrons. It being recognized that $6.25 \times 10^{18}$ electrons per second represents one ampere of current, the relative sensitivity of the instant device will become apparent. As a consequence, the mechanical structuring of the mounting arrangement for the crystal within the probe 12 is of critical importance as is the technique for detecting and treating these significantly small charges representing gamma ray interactions.

Figure 2:
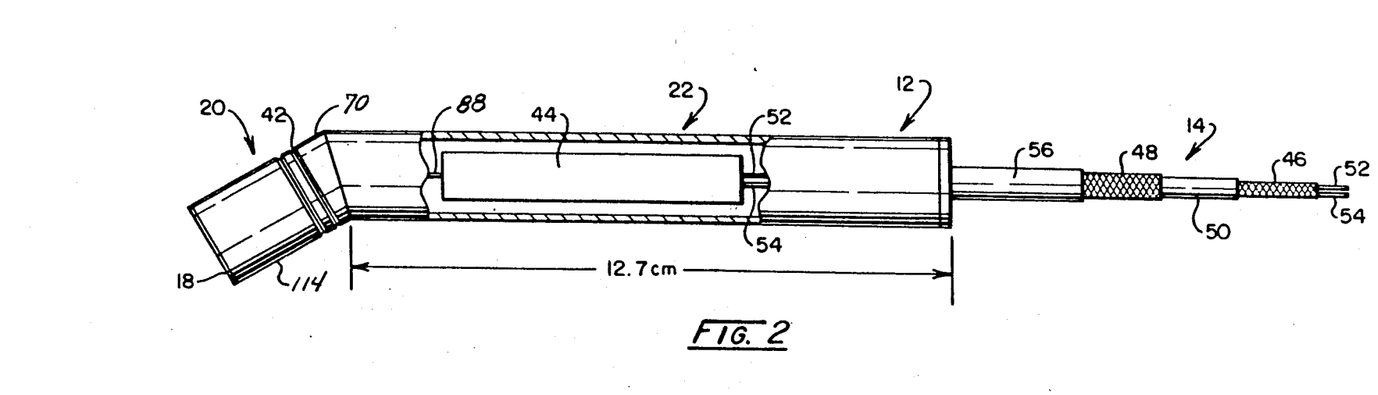
FIG. 2 is a side elevational view of the probe instrument shown in FIG. 1 with portions broken away to reveal internal structure.

Looking to FIG. 2, a more detailed representation of the probe device 12 is revealed. The angular orientation of the front portion 20 is shown having the noted 30° cant with respect to the central axis of the hand gripped portion 22. Device 12 is small having an overall length of about 19 cm and portion 22 having a length of about 12.7 cm. The overall diameter of the cylindrical structure 12 is about 1.9 cm. Front portion 20 is formed having a groove 42 for retaining various "clip-on" devices. Experience to the present, utilizing low energy radiolabeling and achieving very high sensitivity on the part of the probe has removed the need for forward collimation. The hand grip portion 22 carries a preamplifier on an elongate circuit board as represented in general at 44. Depending upon the energies of radiation encountered, the probe 12 structure is formed of an electrically conductive and thus shielding material which functions to attenuate radiation.

Cable 14 supplies power to the preamplifier of the probe, as well as bias to the crystal and functions to transmit the preamplifier treated output signals. Cable 14 includes tin copper cladding components 46 and 48 which are mutually insulated and spaced by a silicon rubber tube 50 which is somewhat loose to permit flexure. The innermost leads of the arrangement at respective lines 52 and 54 carry the output signals from the preamplifier 44 and a bias signal, for example 30 volts, for application to the rear side of the crystal within the device 12. Clad 46 carries a 12 V power supply for the preamplifier circuit, while outer clad 48 carries ground for the system. An outer silicon rubber cover then is provided at 56.

Figure 3:
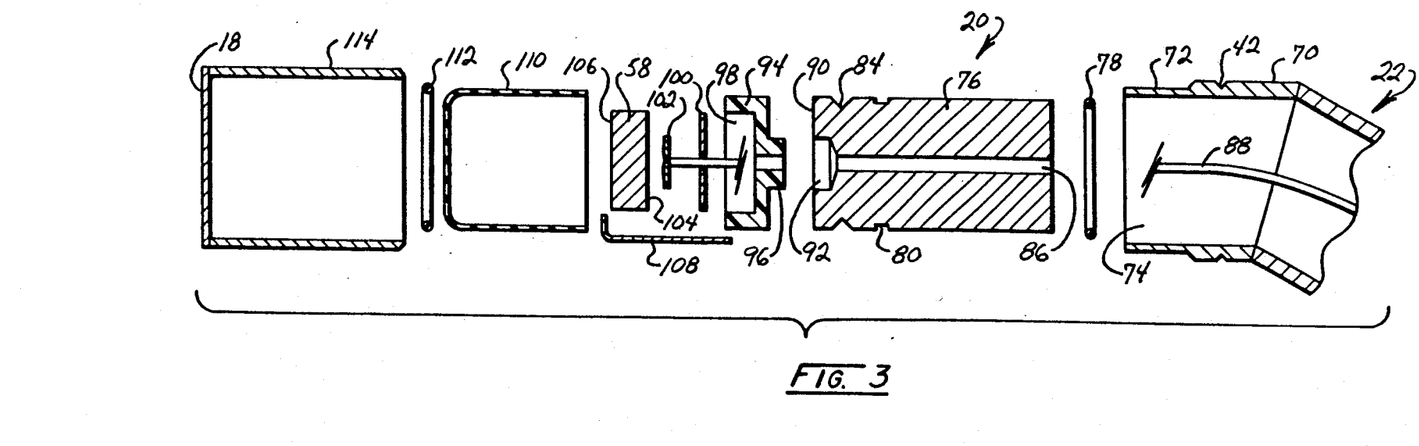
FIG. 3 is an exploded view of the forward assemblage of the instrument of FIG. 2.

Looking to FIG. 3, an exploded detail of the nose or forward portion 20 of probe 12 is provided. This portion 20 retains a cadmium telluride crystal 58 in a light-tight and mechanically secure orientation while maintaining necessary ground and bias conditions upon it. Generally, such crystals as at 58 will have a rigidity or physical consistency somewhat similar to chalk and are formed having very light gold coatings on their surfaces. Thus, the mounting of such delicate crystals and their operation within a probe instrument as at 12 requires a highly refined design architecture. However, it is also important that the structure of the probe 12 be such as to permit its fabrication in a reasonably practical manner.

Figure 4:
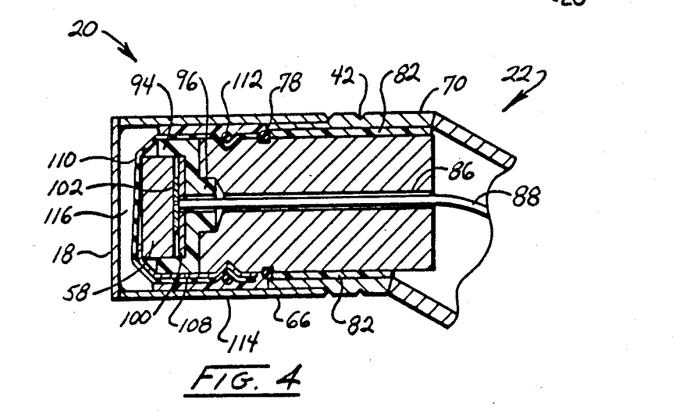
FIG. 4 is a sectional view of the forward portion of the instrument embodiment represented in FIG. 3.

FIG. 3 shows the hand-graspable portion as at 22 extending to a supporting tubular portion 70. The forwardly disposed tubular region of portion 70 including cylinder connector surface 72 are configured having an internal diameter defining a cavity or chamber 74. Cavity 74 receives a generally cylindrically shaped slug or blocking arrangement 76 along with an elastomeric retainer layer which retains the slug 76 within the cavity while spacing its outer cylindrical surface from the interior wall of portion 70 an amount sufficient to provide a shock mounting arrangement. This elastomer may be provided, for example, as a rubber epoxy material. To achieve spacing from the noted interior wall and facilitate mounting, an elastomeric ring such as an O-ring is provided as at 78 which serves to hold the slug 76 in an appropriate position while the elastomeric rubber epoxy sets. The O-ring 78 is slid over the copper outer cylindrical surface of slug 76 so as to nest in a rectangular groove 80 formed therein. Looking additionally to FIG. 4, the O-ring 78 is seen in assembled position and the elastomeric retaining layer is shown at 82. Slug 76 is formed of copper or tungsten to attenuate radiation impinging from a rearward direction into the probe instrument 22 and further includes a V-shaped groove 84 extending thereabout. A central bore 86 extends through the slug 76 to carry an insulated lead 88. Lead 88 functions as a bias-signal transmission wire leading to the physically adjacent preamplification stage 44. The forwardmost face of slug 76 provides a base support surface as at 90 which is counterbored at 92 so as to provide an improved connection with a plastic electrically insulative cup or support 94 having a rearwardly disposed cylindrical portion 96 which is nestable within the bore 92. Cups as at 94 may, for example, be formed of a polycarbonate material such as Lexan or the like and, preferably, are adhesively attached to the base support surface 90 and counterbore 92 by a compatible adhesive. Cup 94, as before, includes a central cylindrical cavity 98 which receives and supports an assemblage including a resiliently compressible shock cushion layer 100 as an initial component. Layer 100 may, for example, be formed of a non-woven Teflon (polytetrafluoroethylene) cloth of marketed under the trade designation "GORETEX" having a thickness, for example of about 0.020 in. The layer 100 is provided having an opening in the middle thereof for receiving the lead 88. In general, this lead 88 is formed as a multistrand type and the strands thereof are attached to a small disc 102 of adhesive copper tape. This disk 102 serves to electrically couple lead 88 to and apply a biasing voltage to the rearwardly disposed face 104 of crystal 58. The forward face of crystal 58 as at 106 is electrically grounded by a copper ground strap 108 which extends rearwardly to provide electrical grounding communication with the exterior of copper slug 76. The assemblage of crystal 58, copper adhesive tape or disk 102, shock cushion layer 100, and cup 94 are compressively retained together by an elastomeric retainer 110 which may be provided, for example, as a common finger cot. This sheath of electrically insulative elastomeric material is rolled over the assemblage and retained in position by a resilient band such as a resilient O-ring 112. O-ring 112 nests in the earlier-described V-shaped circumferential groove 84 to retain the sheath 110 in position. The entire assemblage of slug 76 and those parts compressively retained in position by the sheath 110 and O-ring 112 may be maneuvered during the assemblage employing rubber epoxy layer 82 to provide appropriate spacing accommodating for variations in component thicknesses, for example the thickness variations which may be encountered with crystal 58. The forward assemblage including tube 114 and window 18 then is positioned over surface 72 and cemented in place, for example, with a conductive silver epoxy cement. Note in FIG. 4 that the assemblage is so oriented that a dead space 116 is created between the forwardly disposed surface 106 of crystal 58, as associated with retainer sheath 110, and window 18. This dead air space provides an enhancement of acoustic isolation of the crystal 58.

As represented at circuit 44 in FIG. 2, in order to carry out the treatment of the very faint charges which are evolved due to gamma interaction with crystal 58, it is important that the preamplification function take place as close as possible to the situs of the interaction. Because of the operational need in surgery for the 30° cant of the central axis of the forward portion 20 with respect to the corresponding axis of the rearward support portion 22 of the probe 12, the small length of transmission wire 88 is required. Because extremely small charges of current are involved in the range of 300–600 attocoulombs, a preamplification stage which performs to achieve a very high gain is called upon but one which performs with low noise generation. In effect, the preamplification stage of the instant apparatus is one achieving a voltage amplification, for example, on the order of about 25,000.

Crystal 58 is maintained in a carefully electrically shielded, acoustically dead and light-tight environment.

The outer surface of front portion 20 of the probe instrument 12 is an electrically conductive tube or collar 114 formed, for example, of copper so as to provide a laterally disposed electrical shield, as well as an attenuator for radiation of the energy range contemplated. The forward edge of the tube 114 is closed by the window 18 which is formed, for example, of a silicon-aluminum alloy about 0.015 in. thick soldered thereto. As noted above, the window 18 is selected to permit entry of very low level emissions of gamma radiation. Thus, it is structure to permit the full forward face of crystal 106 to be exposed to such radiation. Even though the window 18 is relatively broad in extent, the capability of the instrument 12 to differentiate the interface between tissue carrying radiolabelled antibodies and the like and those not carrying these labels is quite accurate to the extent that collimation to achieve close differentiation typically is not required.

Figure 5:
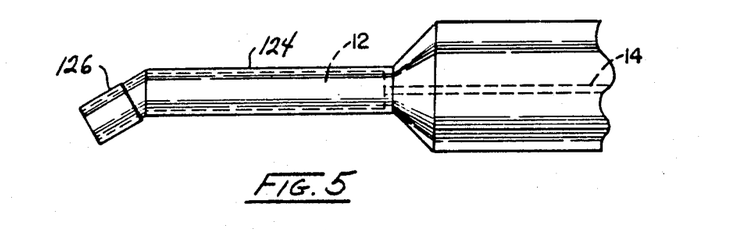
FIG. 5 is a side view of the probe instrument of FIG. 2 showing its employment with a sterile cover or sheath.

A technique which both simplifies cleaning the instrument and maintaining its sterile condition involves the use of a disposable plastic cover which fits over the probe device 12 and which is formed of a polymeric material which is readily produced in a sterile state. Thus, prior to an operation, the surgical personnel will slide the probe within the cover or sheath. The addition of the polymeric surface aids in the control of vibration induced noise as well as representing an ideal technique for maintaining the requisite sterile condition for the device. Looking to FIG. 5, the instrument 12 is shown in dashed line fashion with a polymeric cover 124. The cover 124 includes a nose portion 126 formed of a tough plastic having a thickness, for example, of 0.020 inch. This will protect the cover 124 from tearing or the like when used in the rigorous activities of surgery. From the nose portion 126 the sheath may extend rearwardly a sufficient length to cover the signal transmission components as at 14 for a sufficient distance to assure sterile integrity.

Figure 6A:
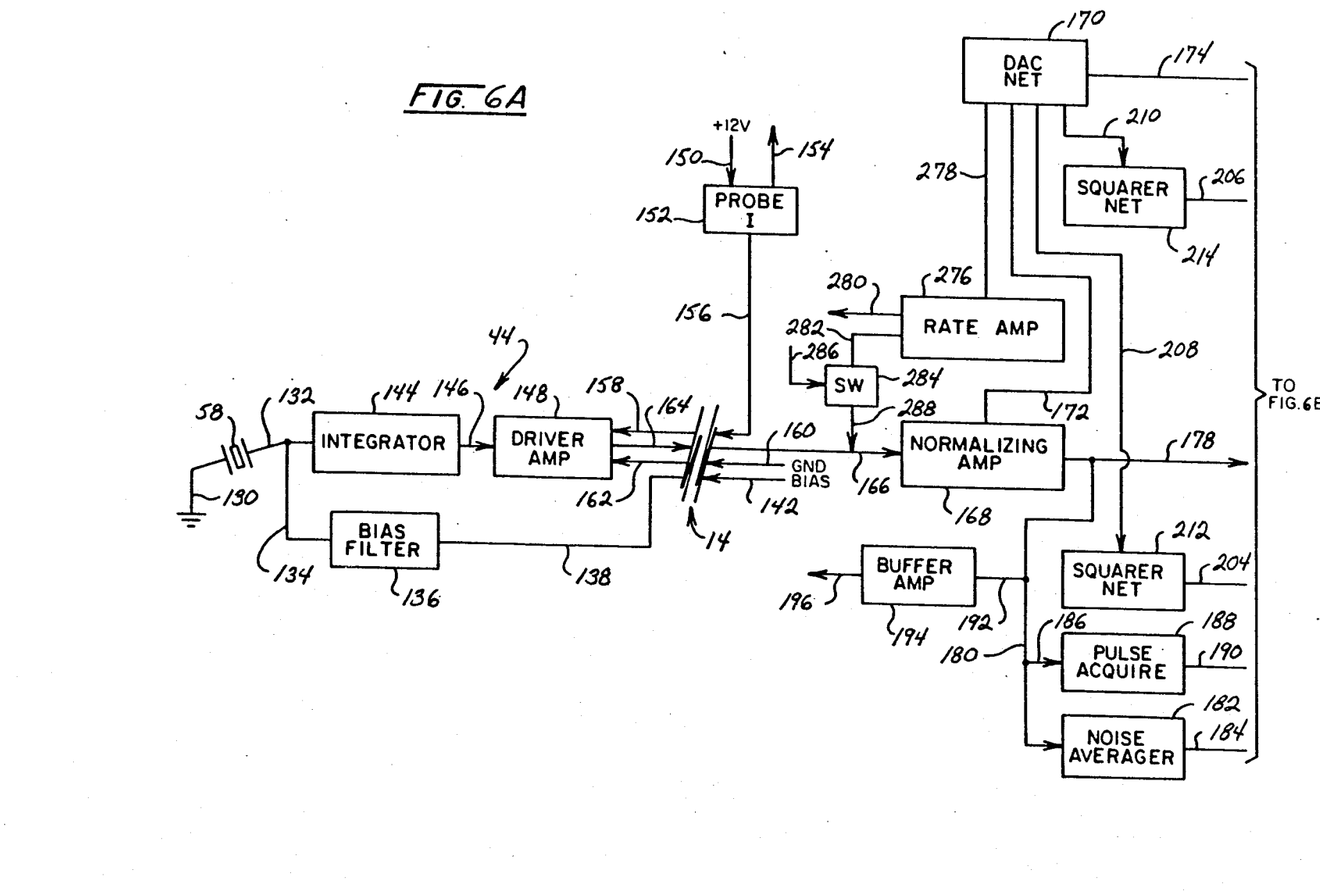
FIGS. 6A and 6B combine as labeled to form a block diagram of the functional components of the control system associated with the probe of the invention.
Figure 6B:
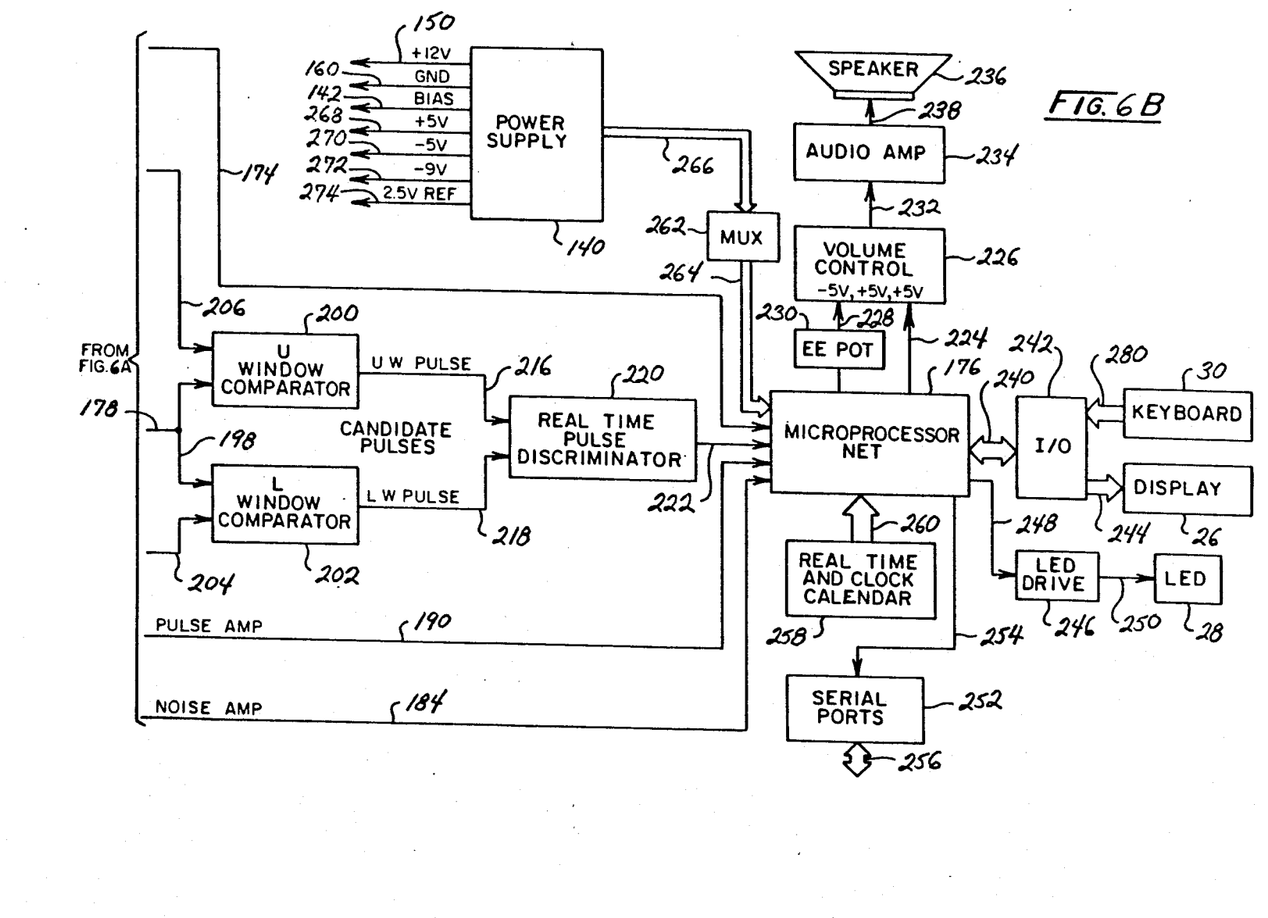

Referring to FIGS. 6A and 6B, a block diagrammatic representation of the instrumentation circuitry is revealed. In FIG. 6A, the cadmium telluride crystal 58 is shown having one face coupled to ground through line 130, while the opposite, biased face thereof is coupled via lines 132 and 134 to a bias filter represented at block 136. The input to the filter 136 is represented at line 138 as being applied through the triaxial cable as described earlier at 14 and represented by that numeral herein. Line 138 corresponds with the earlier-described line 52 in FIG. 2. This bias emanates from a power supply shown at block 140 in FIG. 6B and represented at line 142.

Line 132 from the crystal 58 is shown extending to an integrator stage 144 of the preamplifier 44. The integrated valuation of detected radiation disturbance then is shown directed as represented by line 146 to a driver-amplification network shown at block 148. A 12v power supply is provided from the power supply 140 (FIG. 6B) as represented at line 150 which, as shown in FIG. 6A, is directed to a probe current network represented by block 152. Under microcomputer control as represented by line 154, the network 152 develops signals, for example, determining whether the probe instrument 12 has been properly connected to the console 16. Delivery of the 12 V power supply for the preamplifier stage 44 is represented at line 156 as extending to the driver amplifier from cable 14 via line 158. Line 158 corresponds with the clad 46 described in conjunction with cable 14 in FIG. 2.

Ground to the instrument 12 also is developed from the power supply block 140 as represented at line 160 shown in FIG. 6A as extending to cable 14 and via line 162 to the instrument preamplification components 44. Line 162 corresponds with the earlier-described clad at 48 in FIG. 2.

The output of the preamplification circuit 44 is represented at line 164 extending through the cable representation 14 corresponding with the earlier-described line 54 in FIG. 2. Line 164 extends from the cable 14 as line 166 to the input of a normalizing amplifier represented at block 168. The network represented by block 168 functions to amplify or attenuate, i.e. scale the noise characteristic of any given instrument 12 and normalize the value thereof or render it consistent for later comparison stages. Generally, for example, the 27 kev energy level gamma ray generated pulses in the system will be about five times higher than noise levels. Normalizing amplifier network 168 will establish those noise levels at some predetermined level, for example, 200 millivolts and the resultant proportional valid gamma related pulses will become about one volt high for purposes of ensuing comparison functions. It may be observed that the amplifier network at block 168 is shown controlled from a digital-to-analog converter network represented at block 170 via line 172. Network 170, in turn, is controlled from line 174 extending, as shown in FIG. 6B, to block 176 representing a microcomputer network. The normalized output developed from network 168 is presented along lines 178 and 180 to a noise averager circuit as represented at block 182. This network 182 determines an average amplitude value for the noise of a given system with a given instrument 12 and provides a corresponding signal as represented at line 184 (noise amp) which is employed as above-described as information used by the microcomputer 176. This information, in addition to being employed with the normalizing amplifier network represented at block 168 may be employed to develop a low window valuation for the comparison function.

Line 180 also extends via line 186 to a pulse acquire network represented at block 188. This network functions, when activated by the microcomputer represented at block 176, to acquire the value of the highest pulse amplitude witnessed at line 186. Periodically, this information then is transmitted to the microcomputer at block 176 as represented by line 190. Representing a form of peak detector, the network is sometimes referred to as a "snapshot circuit". Also produced from line 180, as at line 192 and block 194 is a buffer amplifier which will provide at line 196 an output representing received pulses which may be made available at the rearward portion of console 16 for conventional radiation evaluation purposes.

Line 178 extends, as shown in FIG. 6B at line 198, to one input of an upper window comparator represented at block 200 and a lower window comparator illustrated at block 202. The threshold level for comparative purposes employed by the network at block 202 is shown asserted from line 204 and, preferably, is developed by the logic of microcomputer network 176 at a level just above the noise amplitude signals generated from line 184. Of course, manual setting of such windows can be carried out. In similar fashion, the upper window of acceptance for valid gamma ray interaction is established from a corresponding line 206. This threshold setting may be made from the information taken from pulse acquire network 188.

Returning to FIG. 6A, the upper window and lower window threshold selections are made under the control of the microcomputer network at block 176 as controlled from the digital-to-analog network shown at block 170. It is characteristic of such networks as at block 170 to provide an output which is comprised, for example, of 256 steps of varying amplitude. The percentage of incrementation from step-to-step will vary somewhat over the range of voltage values provided. Accordingly, the outputs from this conversion network at block 170, as at lines 208 and 210 are directed to squarer networks shown, respectively, at blocks 212 and 214. These networks function to square the current outputs at lines 208 and 210 and thus achieve a uniform percentage incrementation of the threshold defining outputs at lines 204 and 206.

Returning to FIG. 6B, the outputs of the comparator networks shown at blocks 200 and 202 represent candidate pulses which may be above or below the given thresholds and are identified as being presented as a "UW pulse" and an "LW pulse" along respective lines 216 and 218. These lines are shown directed to a real time pulse discriminator network represented at block 220 which carries out Boolean logic to determine the presence or absence of valid pulses. Valid pulses are introduced to the microcomputer network 176 as represented by line 222.

The microcomputer represented at block 176 performs under a number of operational modes to provde both audio and visual outputs to aid the surgeon in locating and differentiating tumorous tissue. In the former regard, as represented at line 224 and block 226, a volume control function may be asserted with amplitude variations controlled from a solid-state form of potentiometer as represented at line 228 and block 230. Further, a "siren" type of frequency variation may be asserted as represented at line 232 to an audio amplification circuit represented at block 234 for driving a speaker as represented at 236 and line 238. With the noted siren arrangmeent, the frequency output from speaker 236 increases as the instrument 12 is moved closer to the situs of concentrated radiation. Of course, conventional clicks and beeps can be provided at the option of the operator.

The microcomputer network 176, as represented by arrow 240 and block 242 also addresses an input-output network which, as represented at arrow 244, functions to provide a pulse count output of varying types as well as outputs represented volume levels, pulse height, noise levels and battery status. Visual readout is represented in FIG. 6B as a block with the same display 26 numeration as described in conjunction with FIG. 1. Similarly, the input-output function represented at block 242 provides appropriate scanning of the keyboard or switches described in conjunction with FIG. 1 at 30 and represented by the same numeration in FIG. 6B. During the counting operation, the microcomputer network 176 functions to control a light emitting diode drive network represented by block 246 from line 248. The drive network represented at block 246 is shown providing an input, as represented by line 250 to the dual LED display as described at 28 in FIG. 1 and represented in block form with the same numeration. This readout provides a red light when a gamma ray is detected and a green light during the counting procedure in general. A serial output port of conventional variety also is provided on the console 16, such ports being represented at block 252 being addressed from the microcomputer at block 176 from line 254 and having output and input components represented by arrow 256. A real time clock-calendar having a non-volatile memory also may be provided in conjunction with the functions of the microcomputer network 176 as represented by block 258 and arrow 260. Further, the microcomputer may be employed to monitor the performance of the power supply represented at block 140. This is shown being carried out by the interaction of the microcomputer network with a multiplexer represented at block 262 and having an association represented by arrows 264 and 266. It may be observed that the power supply also provides +5 V sources for the logic level components of the circuit as represented by line 268; a −5 v source at line 270, as well as a −9 v reference at line 272 for display 26 drive and, finally, a 2.5 v reference as represented at line 274 to provide reference input to the analog circuitry described alter herein.

Returning to FIG. 6A, the microcomputer network as represented at block 176 also provides an input to the digital-to-analog conversion network represented at block 170 which corresponds with the instantaneous pulse rate and this information is conveyed to a pulse rate amplifier network represented at block 276 via line 278. The resultant output as represented at line 280 may be provided, for example, at the rear of the console 16. This circuit represented at block 276 also may be employed to generate a calibrating pulse for testing the downstream components of the system. Thus, the microcomputer applies a predetermined pulse level through the digital-to-analog conversion network at block 170 for presentation to the amplifier network represented at block 276. The resultant output at line 282 is selectively switched as represented by block 284 to define pulse width from the microcomputer input at line 286 to the calibrating pulse at line 288.

Since certain changes may be made in the above-described system and apparatus without departing from the scope of the invention herein involved, it is intended that all matter contained in the description thereof or shown in the accompanying drawings shall be interpreted as illustrative and not in a limiting sense.

We claim:

1. An instrument for detecting and locating sources of radiation emission having predetermined energy levels, comprising:

a housing having interior walls defining an interior cavity and first portion having sidewalls formed of select gamma radiation attenuating material and exhibiting an electrical shielding effect and extending to a forward opening positionable proximate said source, and a hand graspable second portion extending from said first portion;

window means for permitting transmission of gamma radiation of energy level at least as low as 27 kev through said forward opening while blocking the passage of light;

blocking means formed of material selected for attenuating gamma radiation of said predetermined energy levels, having an outer surface, supportable within said housing and having a portion extensible within said housing first portion to a base support surface;

elastomeric means intermediate said housing and said blocking means for retaining said blocking means spaced from said housing interior wall;

electrically insulative support means mounted upon said blocking means base support surface and having a mounting surface positioned outwardly from said base support surface;

a resiliently compressible shock cushion layer positioned in adjacency over said insulative support means and having an outwardly disposed surface;

a gamma radiation responsive crystal having a rearwardly disposed surface positioned in adjacency with said shock cushion layer and having a forwardly disposed surface;

grounding means for electrically grounding said crystal forwardly disposed surface;

biasing means for applying an electrical bias to said crystal rearwardly disposed surface;

elastomeric retainer means positioned over the assemblage of said support means, said shock cushion layer, and said crystal for effecting their compressed mutual association;

retaining means for positioning said housing first position over said assemblage and said blocking means portion such that said crystal forwardly disposed surface is spaced from said window means an amount establishing a dead air space therebetween.

2. The instrument of claim 1 in which said elastomeric retainer means is a thin sheath mountable over said assemblage.

3. The instrument of claim 1 in which said resiliently compressible shock cushion layer is a non-woven polytetrafluoraethylene cloth.

4. The instrument of claim 1 in which said elastomeric means is a layer of rubber epoxy adhesive.

5. The instrument of claim 1 including a disposable, sterile, thin polymeric cover positionable over said housing for isolating said housing from contaminants and presenting a sterile instrument exterior for surgery.

* * * * *